Figure 1:
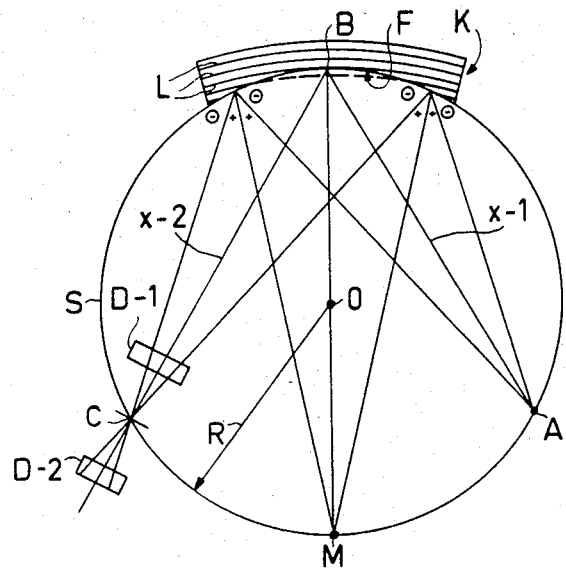

United States Patent [19]

Brinkgreve et al.

[11] Patent Number: 4,637,041
[45] Date of Patent: Jan. 13, 1987

[54] KINEMATIC X-RAY ANALYSES APPARATUS

[75] Inventors: Peter Brinkgreve, Waalre; Diederik C. Koningsberger, Eersel, both of Netherlands

[73] Assignee: Technische Hogeschool Eindhoven, Eindhoven, Netherlands

[21] Appl. No.: 588,280

[22] Filed: Mar. 12, 1984

[30] Foreign Application Priority Data

Mar. 15, 1983 [NL] Netherlands ............. 8300927

[51] Int. Cl.$^4$ ............... G01N 23/20; G01N 23/207; G21K 1/06
[52] U.S. Cl. ............................. 378/71; 378/79; 378/84; 378/81
[58] Field of Search ............... 378/71, 79, 70, 84, 378/80, 81

[56] References Cited

U.S. PATENT DOCUMENTS

| | | | |
|---|---|---|---|
| 2,898,469 | 8/1959 | Rose | 378/83 |
| 3,051,833 | 8/1962 | Schumacher | 378/80 |
| 3,123,710 | 3/1964 | Neuhaus | 378/84 |
| 3,384,756 | 5/1968 | Hasler et al. | 378/84 |
| 3,445,653 | 5/1969 | Tomura | 378/82 |
| 4,446,568 | 5/1984 | Williams et al. | 378/84 |

FOREIGN PATENT DOCUMENTS 0072050  5/1982  Japan ...................... 378/81

Primary Examiner—Craig E. Church
Assistant Examiner—Charles Wieland
Attorney, Agent, or Firm—Paul R. Miller

[57] ABSTRACT

In an X-ray analysis apparatus, a moving mechanism is provided by a main guide member along which a main slide device can be displaced. Rotatably connected with the main slide device is a detector guide member along which a detection slide device is displaced. The main slide device, as well as the detection slide device, and an axis of rotation relative to an end of the main guide member are connected to a common central axis by respective arms which can be mutually rotated with them. The main slide device and the detection slide device can each be equipped with a drive motor where the motor for the main slide device is preferably driven first, and the motor for the detector slide device is driven by signals derived from displacing the main slide device. The rotatable arms ensure an optimum orientation of a crystal holder incorporated onto the main slide device, and a detection holder incorporated onto the detector slide device with respect to each other and with respect to a point of focus of an X-ray source.

14 Claims, 4 Drawing Figures

KINEMATIC X-RAY ANALYSES APPARATUS

The invention relates to an X-ray analysis apparatus with an X-ray source, a sample holder, a crystol holder, an X-ray detection device and with a movement mechanism for the displacement and orientation of different components with respect to each other.

Such an X-ray analysis apparatus, in the form of an X-ray diffraction apparatus, is known from U.S. Pat. No 2,898,469.

For apparatus in which accurate angle settings and/or distance settings are needed, such as for X-ray diffraction with a high resolving power, for the examination of tension in, for example, workpieces, for phase measurements on alloys, for X-ray absorption measurements such as, for example, exafs (extended X-ray absorption fine structure) measurements, for crystal structure measurements in diffusion and/or implantation and suchlike, the accuracy and reproducibility of the known movement mechanism is frequently inadequate.

In such an apparatus, adapted for measurements of, for examle, exafs, it is advantageous to use, for example, a Johannson crystal as a monochromator, as described together with other types of crystals in the book "Principles and Practice of X-ray Spectrometer Analysis" by E. P. Bertin, Plenum Press, pp. 148–160. Here a crystal that is bent according to Johannson and ground out to a radius of curvature corresponding to the radius of curvature of a Rowland circle, on which Rowland circle in these measurements a point of focus and a sample to be irradiated are positioned at equal distances along an arc from the center of the monochromator crystal. The angle of incidence $\theta$ of the radiation on the monochromator crystal is varied for scanning the sample. This could easily be achieved by moving the point of focus and the sample towards each other along the Rowland circle in the above-mentioned configuration, while maintaining the equal distances along the arc. It is difficult to achieve a reasonably exact displacement of the point of focus and, along with it, the X-ray source. For this reason the point of focus is fixed and the position and orientation of the sample and the monochromator crystal are varied. Here, the Rowland circle itself is necessarily also moved in such a way that it passes through the point of focus, whereby the center of the Rowland circle describes a circular orbit around the point of focus. In addition, the direction of the monochromator crystal and the sample or a detector or a detector system must constantly be adjusted. A mechanism for the displacement and orientation of the various components for this, and more generally for a linear spectrometer, is, in particular, the subject of the invention.

The object of the invention is to provide an X-ray analysis apparatus in which the movement mechanism for the mutual displacement and orientation of components is executed in such a way that it permits an accurately determined and readily repoducible adjustment of the components with respect to each other. To this end, an X-ray analysis apparatus of the kind mentioned in the introduction, according to the invention, is charcterized by the fact that the movement mechanism is equipped with a main side which can be displaced along a main guide, a detection guide rotatably connected with the main slide with a detection slide which can be displaced along the detection guide and with a detection-to-center arm, a crystal holder-to-center arm and a source-to-center arm with these three arms being mutually rotatable around a common central axis and being rotatably connected with, respectively, the detection slide, the crystal holder and with an axis through a point of focus.

Since an X-ray analysis apparatus in accordance with the invention incorporates a main guide, preferably with an adjustable threepoint support which, in principle, carries all the components, the demands to be met by the surface of a table for carrying the apparatus are less stringent than usual. Since the main slide is driven by a friction transmission, a continuous, backlash-free and extremely reliable displacement of the main slide is ensured. The displacement of the main slide can easily be measured with a high degree of accuracy, for example by adding an appropriate ruler, or the displacement distance can be controlled.

In a preferred embodiment the coupling between the main slide and the main guide is kinematically determined, and to this end the main slide contains, for example, five pairs of supporting points with respect to the main guide which are attached in pairs to guide surfaces of the main guide. In particular, the hinges required for the pre-tensions to be applied here are realised by cutting slits in a top plate and a bottom plate of the main slide which permit an elastic hinging in the surface of the plates.

In a preferred embodiment of an apparatus in accordance with the invention, particularly suitable for making exafs measurements, an anode impingement point of an X-ray tube forms the point of focus, the crystal holder contains a bent and preferably ground out monochromator crystal and on the detection slide there is a sample to be irradiated, preferably with a beam detector on either side of it, looking in the direction of the beam path. In this respect, the point of focus, the monochromator crystal and the sample, or an entry slit of a first detector, all lie on a Rowland circle determined by the centrally positioned arms. In this respect, a spindle through the point of focus is implemented in a mounting block that, for example, is connected to the main guide via a ballbearing connection. Through this spindle, the source-to-center arm is similarly connected to the main guide via the mounting block with the point of focus thus coinciding with the axis of rotation of the source to-center arm.

With the arrangement of a monochromator crystal in the crystal holder, a sample to be examined and seen in the direction of the beam path, preferably placed both in front of and behind it, and an X-ray detector on the detection slide, a high quality apparatus for exafs measurements is achieved. The requirement for the adjustment of the distance between the focal point of the source and the monochromator crystal which is critical in this respect can be amply fulfilled here. For example, by adding a ruler to the main guide and the detection guide that distance can also be measured exactly. Measuring signals obtained from the ruler on the main guide can be used for adjusting the sample on the detection slide along the detection guide at an equal distance with respect to the monochromator crystal.

With, for example, a sample to be irradiated at the side of the point of focus, an analysing crystal in the crystal holder on a crystal changer instead of the crystal holder, and an X-ray detector mounted on the detection slide, an extremely accurate linear spectrometer is achieved. Here, too, it is practical to allow the radiation source, in this case the sample to be irradiated, to occupy a fixed position.

With a monochromator in line with the main guide, a sample to be examined in the crystal holder and a detector mounted on the detection slide, a diffractometer is achieved with an accurate positioning for the relevant components, and hence, with the possibility for performing measurements with a high resolving power such as, for example, for texture and phase measurements.

The adjustment of measuring variants in the X-ray tube with respect to the focal spot on the anode and hence of the point of focus, and for variation in the angle between the surface of the anode and the beam, can be achieved by positioning the X-ray tube with respect to the mounting block. For adjustment of the radius of curvature of a monochromator crystal to be placed in the holder, the crystal holder arm, the detector arm and the centrally positioned arm, in a preferred embodiment, are made adjustable in length or are easily exchangeable.

Figure 2:
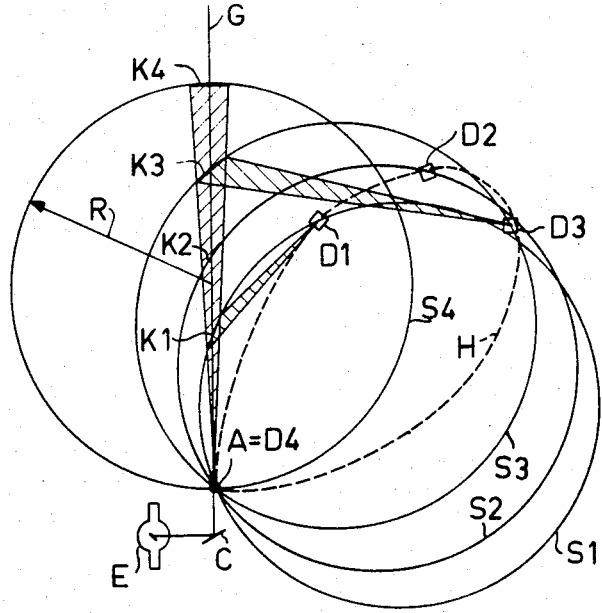
Figure 3:
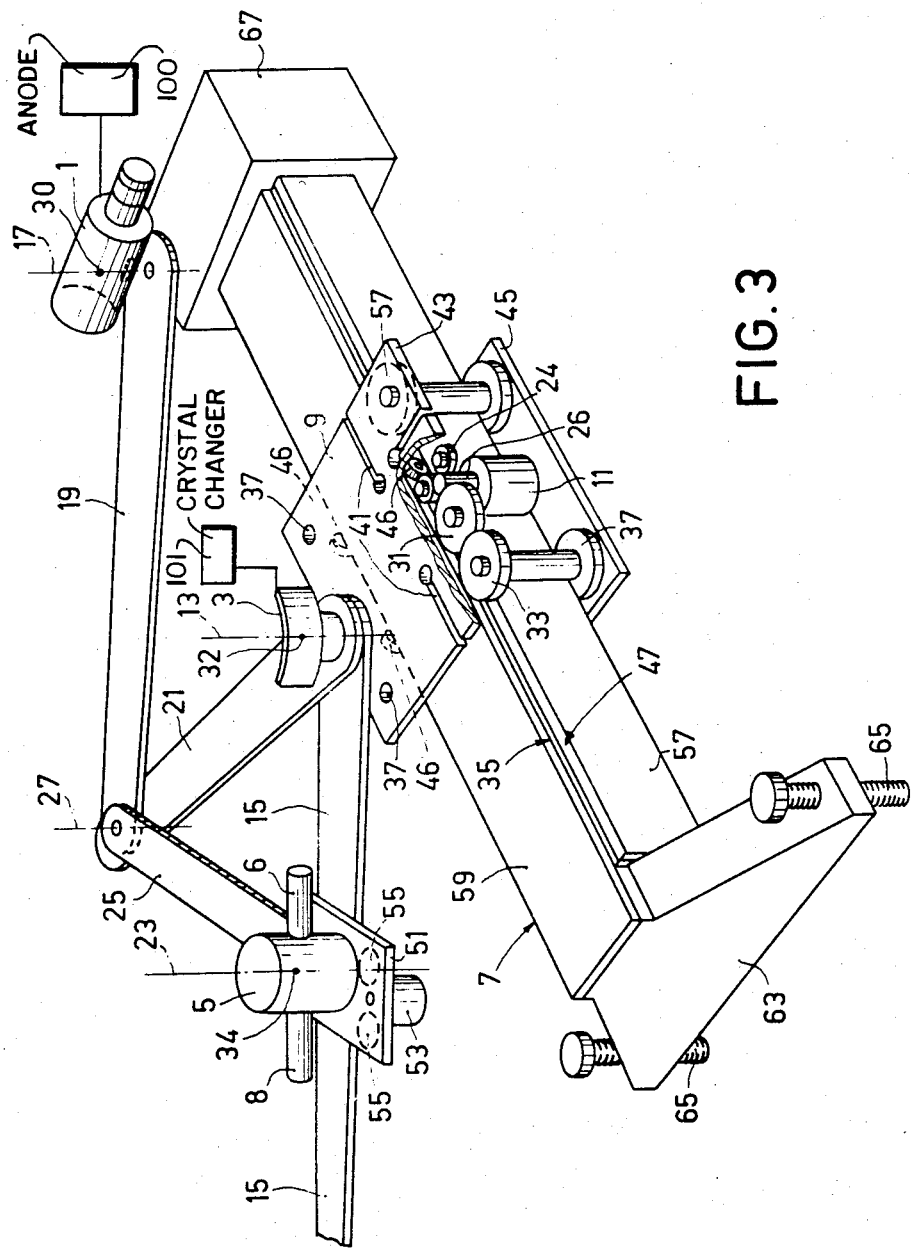
Figure 4:
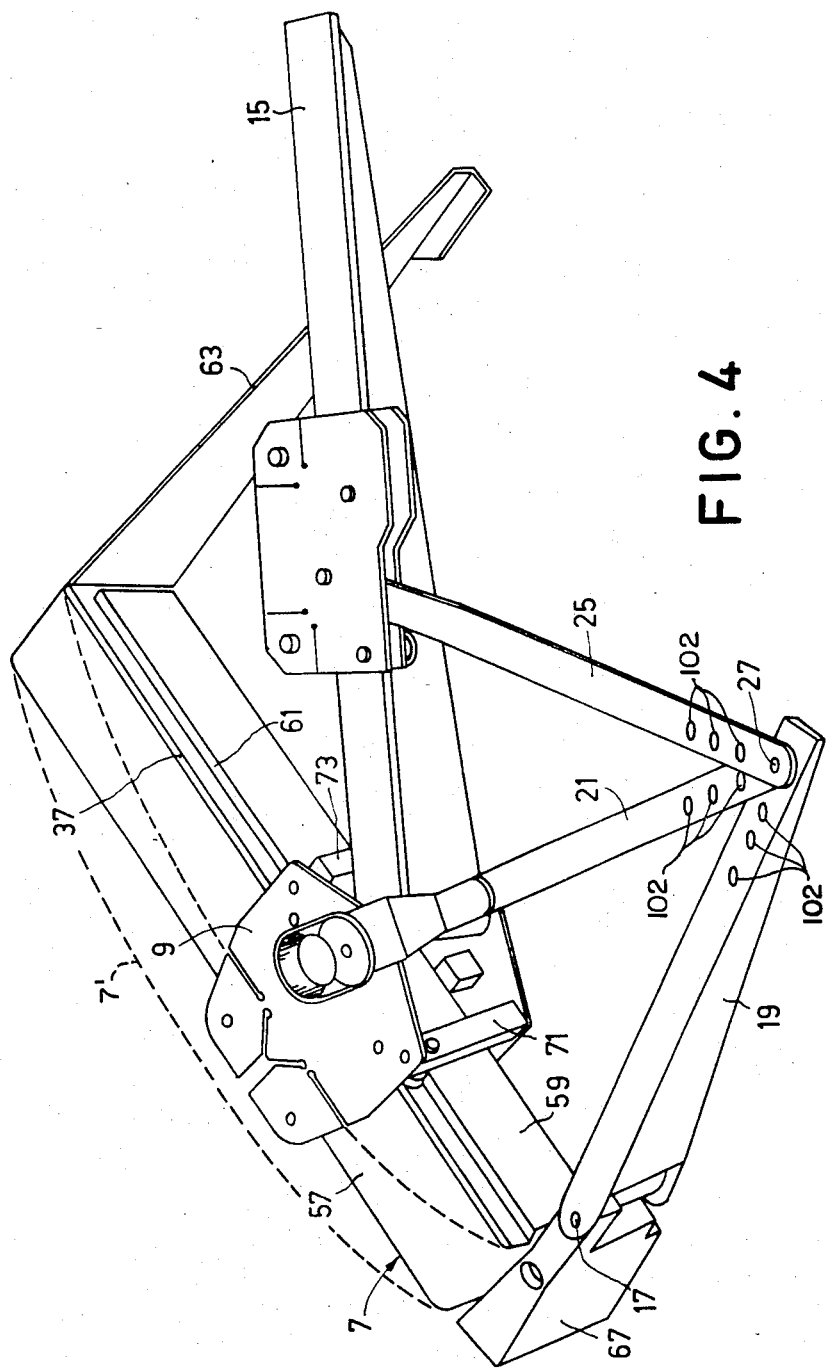

Some preferred embodiments in accordance with the invention will be described in further detail below on the basis of the drawing. In the drawing:

FIG. 1 shows the beam path in an X-ray analysis apparatus, for example for exafs measurements, with a fixed position of all components FIG. 2 shows a series of positions which the components of such an apparatus occupy during a measuring cycle, FIG. 3 shows a schematic diagram of an X-ray analysis apparatus in accordance with the invention, and FIG. 4 shows a more detailed sketch of a movement mechanism for the invention.

FIG. 1 shows the beam path for a fixed measuring position of the various components of an apparatus intended, for example, for exafs measurements with the aid of a Johannson crystal as the monochromator crystal. The Johannson crystal K is bent with a radius of curvature 2R, as a result of which the crystal surfaces L running parallel to the surface of the crystal are also bent with that radius of curvature. A hollow surface F of the crystal bent in this way is ground out to a radius of curvature R. Here R is the radius of a Rowland circle S with the surface F of the crystal coinciding in a measuring position. A beam focus point A, corresponding here to an anode impingement point of an X-ray tube, and a sample C to be irradiated are also placed on the Rowland circle. In this configuration a curvature center point M on the crystal surfaces L lies on the circumstance of the circle and the source point A and sample point C are equidistant from the center on the arc of the Rowland circle. With B as the center of the monochromator crystal we therefore always have AB=BC. Here an X-ray beam x-1 emanating from the point of focus A impinges pinges on the crystal surfaces L of the crystal K over the entire surface F at an equal angle $\theta$ and all the radiation with a wavelength $\lambda$ which at that angle and the crystal surface distance of the crystal surfaces L satisfies the Bragg condition $N\lambda = 2$ d.sin $\theta$ will, after diffraction, impinge upon the sample C focussed in a beam x-2.

For an accurate absorption measurement on the sample it is advantageous to position a detector both in front of and behind the sample. A measure for the incident radiation is then obtained with a detector D-1 and a measure for the radiation permeating the sample is obtained with a detector D-2. In these measurements it can also be advantageous, instead of the sample C, to allow an entry slit in the detector D-1 to coicide with the Rowland circle. The length of the radius R of the Rowland circle is, for example, 50 cm. From the figure it can further be seen that $AB = x = 2R \sin \theta$; with the Bragg condition $N\lambda = 2$ d sin $\theta$ it follows from this that $x = NR\lambda P$, where P is the reciprocal value of d and R is the distance from the crystal surfaces.

There is therefore a proportional relationship between the distance x and the wavelength of the radiation used, and hence an inverse proportional relation between that distance and the energy of the radiation used. For measuring over a required path of the angle of incidence $\theta$, hence over a required wavelength pathor an energy path, with the point of focus A in a fixed position, the monochromator crystal and the sample with the detectors are now displaced and directed with respect to each other, in which respect the center O of the Rowland circle describes a circle around the point of focus A.

FIG. 2 shows some positions which occur in the event of such a measuring path, butnow for a linear spectrometer. The point of focus A is now formed by an entry slit for fluorescent radiation emanating from a part of a sample C to be examined and to be irradiated by a laterally situated X-ray source E. Analysing crystal positions K1, K2, K3 and K4 and detector positions D1, D2, D3 and D4 are shown for each of a series of Rowland circle positions S1, S2,S3 and S4. In the Rowland circle position S4 the detector coincides with the point of focus A. During the measurements, the crystal K makes a linear movement which is directed along a crystal path G and which coincides with the straight line x-1 in FIG. 1. In this respect the detector moves along a path H which corresponds to the path CAM as indicated in U.S. Pat. No. 2,898,462.

An X-ray analysis apparatus in accordance with the invention as drawn in FIG. 3 is particularly suitable for exafs measurements and contains an X-ray source 1, a crystal holder 3 and a detection holder 5 with, here, detectors 6 and 8. In performing measurements these components, as already indicated, are displaced and oriented with respect to each other. To this end, the apparatus contains a movement mechanism with a main guide 7, along which a main slide 9 can be moved, for example, by means of a drive motor 11, which is mounted here on the main slide, but which can also be set up elsewhere. Connected rotatably around a crystal holder axis 13 with the main slide is a detection guide 15. A source-to-center arm 19 mounted rotatably around a focal point axis 17, a crystal-to-center arm 21 mounted rotatably around the axis 13 and a detection-to-center arm 25 mounted rotatably around a detection axis 23 are all rotatably connected with a central spindle 27 which is at the center of the Rowland circle indicated in the previous figures and is perpendicular to its plane. The X-ray source is an X-ray tube of a known type, preferably with a rotating anode 100 if a high radiation density is required, as is the case here. A focal point 30, in practical cases corresponding to a radiation focus on the anode of the X-ray tube 1 is located on the axis of rotation 17. The length of the arm 19 between the focal point axis 17 and the central axis 27 determines the radius of the Rowland circle. The crystal holder axis 13, the detection axis 23 and axis 17 are arranged perpendicular to the plane of the Rowland circle at the focus of the circumference of the Rowland circle. The focal point 30 lcoated on axis 17, the crystal holder point 32 located on axis 13 and a detection point 34 located on axis 23 all lie on that Rowland circle.

The main slide 9 is the primary component driven here. To drive it, a driving shaft 26 of the drive motor 11 clamped-in with, for example, tensioning rollers 24 is coupled, preferably via a friction transmission 31, with a first pre-tensioning roller 33. To obtain accurate positioning of the main slide with respect to the main guide the slide further comprises pre-tensioning rollers 37 which only come into contact with guide surfaces such as 35 and 36 of the main guide. Here pre-tensioning rollers located opposite each other with respect to the main guide, preferably with the addition of slits 41 in cover plates 43 and 46, are coupled together under clamping spring pressure. Corresponding pre-tensioning rollers 46 coming into contact with guide surfaces, such as 47, provide for exact positioning in a direction transverse to first direction. The distance between the focal point 30 and the crystal holder point 32 is primarily set when the main slide is displayed. This adjustment can be carried out with an accuracy of, for example, up to 1 $\mu$m and can be measured by a mechanism coupled with the displacement, for example, a ruler mounted along the main guide. Measuring values obtained from this, converted into electric signals, can be used for displacing a detection slide 51 along the detector guide 15. To this end, the detection slide, like the main slide, is equipped with a drive motor 53 with a friction transmission and pre-tensioning rollers 55 etc. which can largely be the same as those of the main slide, but are not all indicated in the drawing as such. A displacement of the detection slide matching the displacement of the main slide can also be achieved with the aid of a mechanical coupling between the two slides, for example, in accordance with the mechanism described in DE Pat. No. 2,418,372. In these movements, it can be ensured that the distance between the crystal holder 3 and the radiation source 30 is always the same as the distance between the crystal holder 3 and the detection holder 5. During displacements of the main slide 9 the focal point 30, the crystal holder point 32 and the detection point 34 always remain on the circumference of the Rowland circle with, the axis 27 forming the central axis. The center of the Rowland circle is therefore, in fact, displaced during the movement in such a way that axis 27 describes a circle around the axis 17 of the irradiated specimen. The focal point 30 is the only point that remains fixed in one permanent point during measuring movements. As already mentioned, this stems for the practical consideration that an X-ray tube is a heavy component which is difficult to move exactly, partly as a result of the high voltage cable connections needed for it. The displacement of the main slide 9 and of the detection slide 51 can also take place in an open loop. Here the positions of the slides are defined from fixed points on the slides. The inteval between them is given, for example, by the number of steps of a step motor, the number of pulses from a pulsed supply current for a D.C. motor or a similar source. Both for the location of the fixed starting points and for preventing collisions in the apparatus, use can be made of microswitches to be fitted between the slides and the guides with which, for example, the drive motors are switched.

FIG. 4 shows the main components of a movement mechanism suitable for the apparatus described on the basis of FIG. 3 in a different elevation. The main guide 7 contains four guide surfaces 35, already mentioned. These surfaces are formed, for example, by polished side surfaces of metal or plastic strips 57 mounted on the main guide, for example, with, as seen in the drawing, a length of 500 mm, a height of 20 mm and a thickness of 5 mm. Corresponding strips 59 with guide surfaces 61 are fitted for guidance and support in a second direction transverse to the longitudinal direction of the main guide 7. At a first end the main guide 7 is fitted with a support 63 in which, as shown in FIG. 3, adjusting screws 65 are fitted. At an opposite end there is a bearing block 67 by means of which the axis 17 of the irradiated specimen can be localised exactly. To this end, the bearing block 67 is preferably connected to the main guide via a ballbearing. In the correct position, the bearing block 67 can be fixed to the main guide. A third supporting point for the main guide is located on the end of this guide which is near bearing block 67. On a side of the main slide on which the detector guide 15 is mounted the main slide can be equipped with connecting parts 71 and 73. Departing from the solution described on the basis of FIG. 3, the main slide can also be moved forward with a drive motor not mounted on the slide and therefore not moving with it, but in view of the wide range of the main slide that alternative is frequently less attractive. D.C. motors are to be recommended as drive motors because they can be regulated more accurately and are cheaper. The speed of displacement of the main slide can be regulated so that great decelerations or accelerations, which could result in slipping, can be avoided. In the embodiment given here the central arm 19 is connected to the main guide via the bearing block 67. As a result, when aligning the apparatus the focal point can be positioned exactly on a line through the crystal holder point 32 parallel to the main guide. In the case of a linear spectrometer with a radiation entry slit at the site of the point of focus 30, it is frequently more advantageous to connect that slit permanently with the main guide and to position the sample to be irradiated in an adjustable holder, in which case the irradiated X-ray beam must additionally be aimed at the required surface of the sample, albeit less accurately.

Upon displacement of the main slide 9, and a correlated displacement of the detection slide, arms 19, 21 and 25 ensure the correct orientation of the detection holder 5 and the crystal holder 3 with respect to each other and with respect to the point of focus. In order to enable the optimum mutual positioning to be adjusted to possible deviations in, for example, the radius of curvature of a bent monochromator crystal to be mounted in the crystal holder 3, the arms 19, 21 and 25 in a preferred embodiment are made adjustable in length, such as by openings 102 in each of the arms (FIG. 4),--; or so that they can be replaced by arms of different length.

With the exafs measuring method the structure of the crystal line and amorphous materials can be determined with a very high resolving power. In this respect, the advantage of using a bent and ground out monochromator crystal, also sometimes called a focussing monochromator crystal, is that a relatively large part of the X-ray beam is used effectively without any sacrificing of the degree of monochromatism. Here the crystal is bent cylindrically as a Johannson crystal with a radius 2R and is ground out to a radius of curvature R, with R being the radius of the Rowland circle. By taking off the X-ray beam at a relatively small anode angle, for example 6°, a small specimen surface of, for example, 0.05 mm $\times 10^2$ mm is obtained optically. With a relevant crystal size of, for example, 50 mm it is possible to use an X-ray beam with an opening angle of up to approximately 5°. By using both the (111) and the (311) crystal surfaces with equal curvature of a Ge or Si crystal with the K line the elements from As to Pt, and with the L line the elements Tc to Cm, can be measured with an energy range of 2.5 to 25 KeV for the X-ray beam.

As already mentioned, for spectrometry measurements the X-ray source is mounted laterally with respect to the main guide, a sample to be irradiated is placed in line with the main guide and a radiation entry slit is placed at the site of the point of focus 30. The monochromator crystal in the crystal holder is replaced by an analysing crystal which, as is known, can consist of Si or Ge but, for example, can also be of LiF, lead stearate, thallium phthalate, penta erythritol and similar substances. Polychrome radiation emanating from this sample is diffracted by the crystal, depending on the wavelength. In order to be able to measure, for example, the intensity of K radiation of the elements carbon to antimony and the intensity of L radiation of the elements up to and including uranium in such a spectrometer it is frequently desirable to design the crystal holder as a crystal changer, such as designated by 101 in FIG. 3, as a result of which various analysing crystals can easily be brought into a measuring position. The detection holder now contains only one detector, albeit possibly a composite detector, for measuring a wavelength path, to be adjusted by angular variation, of the radiation diffracted by the crystal.

The structure of the main guide with the main slide, as well as that of the detection guide and the detection slide, permit these guides, such as schematically indicated in FIG. 4, to be designed as circular guides. Only a relatively slight adaptation of the main slide is necessary for this. The detector, a sample or an analysing crystal, for example, can then be moved along such guides, with the central arms again ensuring a correct positioning of the various components of the arrangement with respect to each other.

What is claimed is:

1. An X-ray analysis apparatus, comprising an X-ray source, a sample holder, a crystal holder, an X-ray detection device, and moving means for displacing an orienting said crystal holder and said detection device with respect to one another relative to said X-ray source
   wherein said moving means comprises
   a main guide,
   a main slide displaceable along said main guide, said crystal holder being movable with said main slide,
   a detector guide rotatably connected with said main slide,
   a detection slide displaceable along said detector guide, said detection device being mounted on said detection slide,
   a first arm rotatably connected between an axis of rotation of said X-ray source relative to an end of said main guide and a common central axis,
   a second arm rotatably connected between said main slide at said crystal holder and said common central axis, and
   a third arm rotatably connected between said detection slide and said common central axis,
   wherein said main slide includes a first drive motor means for displacing said main slide along said main guide, said drive motor means including a friction clutch and a pre-tensioned roller structure contacting guide surfaces of said main guide, said roller structure being coupled by said friction clutch to said motor means.

2. An X-ray analysis apparatus according to claim 1, wherein said main slide includes mounting plates located at each side of said main guide, said mounting plates having slits to permit elastic deformation, and said mounting plates carrying said roller structure to contact said guide surface at opposite sides of said main guide.

3. An X-ray analysis apparatus according to claim 1, wherein said detection slide includes a second drive motor means for displacing said detection slide along said detector guide, said second drive motor means being controlled by position signals obtained by displacement of said main slide.

4. An X-ray analysis apparatus according to claim 3, wherein said second drive motor means is coupled to said detector guide by a friction clutch and a pre-tensioned roller structure.

5. An X-ray analysis apparatus according to claim 1, wherein said main guide includes a surface having adjusting screws for leveling said main guide.

6. An X-ray analysis apparatus comprising an X-ray source, a sample holder, a crystal holder, an X-ray detection device, and moving means for displacing and orienting said crystal holder and said detection device with respect to one another relative to said X-ray source
   wherein said moving means comprises
   a main guide,
   a main slide displaceable along said main guide, said crystal holder being movable with said main slide,
   a detector guide rotatably connected with said main slide,
   a detection slide displaceable along said detector guide, said detection device being mounted on said detection slide,
   a first arm rotatably connected between an axis of rotation of said X-ray source relative to an end of said main guide and a common central axis,
   a second arm rotatably connected between said main slide at said crystal holder and said common central axis, and
   a third arm rotatably connected between said detection slide and said common central axis,
   wherein said detection slide includes motor means for displacing said detection slide along said detector guide, said drive motor means being controlled by position signals obtained by displacement of said main slide.

7. An X-ray analysis apparatus according to claim 6, wherein said drive motor means is coupled to said detector guide by a friction clutch and a pre-tensioned roller structure.

8. An X-ray analysis apparatus comprising an X-ray source, a sample holder, a crystal holder, an X-ray detection device, and moving means for displacing and orienting said crystal holder and said detection device with respect to one another relative to said X-ray source
   wherein said moving means comprises
   a main guide,
   a main slide displaceable along said main guide, said crystal holder being movable with said main slide,
   a detector guide rotatably connected with said main slide, a detection slide displaceable along said detector guide, said detection device being mounted on said detection slide, a first arm rotatably connected between an axis of rotation of said X-ray source relative to an end of said main guide and a common central axis, a second arm rotatably connected between said main slide at said crystal holder and said common central axis, and a third arm rotatably connected between said detection slide and said common central axis, wherein at least said main guide extends along an arc of a circle.

9. An X-ray analysis apparatus according to claim 8, wherein said main guide includes a surface having adjusting screws for leveling said main guide.

10. An X-ray analysis apparatus according to claims 1, 6, or 8 wherein said main guide includes a carrier block at one end, said carrier block being connected to said main guide by a ball bearing joint.

11. An X-ray analysis apparatus according to claims 1, 6, or 8 wherein said first, second, and third arms are adjustable in length.

12. An X-ray analysis apparatus according to claims 1, 6, or 8, wherein said X-ray source is an X-ray tube having a rotating anode, wherein said crystal holder carries a cylindrically bent monochromator crystal, and wherein said detection device is equipped for carrying a sample, and includes at last one radiation detector.

13. An X-ray analysis apparatus according to claims 1, 6, or 8, wherein said X-ray source is provided outside of said main guide, wherein said sample holder is provided adjacent with said main guide, and wherein a radiation entry slit is provided at said axis of rotation of said first arm.

14. An X-ray analysis apparatus according to claim 13, wherein a crystal changer is provided at said crystal holder.

* * * * *

UNITED STATES PATENT AND TRADEMARK OFFICE
CERTIFICATE OF CORRECTION

PATENT NO. : 4637041

DATED : January 13, 1987

INVENTOR(S) : Peter Brinkgreve ET AL

It is certified that error appears in the above-identified patent and that said Letters Patent is hereby corrected as shown below:

Col 1, Line 5, change "crystol" to --crystal--

Col.1, line 23, change "examle" to --example--

Col. 4, line 22, change "butnow" to --but now--

Col. 6, line 52, delete "--;--"

Signed and Sealed this

Third Day of November, 1987

Attest:

DONALD J. QUIGG

Attesting Officer

Commissioner of Patents and Trademarks